United States Patent [19]

Suresh et al.

[11] 4,234,461
[45] Nov. 18, 1980

[54] OXIDATION CATALYSTS

[75] Inventors: Dev D. Suresh, Macedonia; Noel J. Bremer, Stow; Robert K. Grasselli, Chagrin Falls, all of Ohio

[73] Assignee: Standard Oil Company (Ohio), Cleveland, Ohio

[21] Appl. No.: 891,786

[22] Filed: Mar. 30, 1978

Related U.S. Application Data

[60] Continuation-in-part of Ser. No. 778,658, Mar. 17, 1977, abandoned, which is a division of Ser. No. 602,343, Aug. 6, 1975, Pat. No. 4,052,418.

[51] Int. Cl.[3] .................. B01J 23/10; B01J 21/02; B01J 21/00; B01J 23/16
[52] U.S. Cl. .................... 252/462; 252/432; 252/461; 252/467; 252/468
[58] Field of Search ............... 252/432, 468, 467, 461, 252/469, 471, 475, 476, 462, 470, 472

[56] References Cited

U.S. PATENT DOCUMENTS

| | | | |
|---|---|---|---|
| 3,704,317 | 11/1972 | Yamashita et al. | 252/461 X |
| 3,907,919 | 9/1975 | Lo et al. | 252/472 X |
| 4,010,238 | 3/1977 | Shiraishi et al. | 252/461 X |
| 4,075,231 | 2/1978 | Dolhyj et al. | 252/461 X |

Primary Examiner—Delbert E. Gantz
Assistant Examiner—William G. Wright
Attorney, Agent, or Firm—Joseph G. Curatolo; Herbert D. Knudsen; Larry W. Evans

[57] ABSTRACT

Catalysts comprising the combined oxides of vanadium and at least one element selected from the group consisting of boron, niobium, tantalum, antimony, tungsten and chromium have been found to be especially effective in the oxidation of n-butane, n-butenes and butadiene, or a mixture thereof with molecular oxygen in the vapor phase to yield maleic anhydride. The catalysts of the present invention may be further promoted with additional elements to enhance activity, stability and selectivity. The reaction with n-butane gives an especially pure product in good yield and selectivity.

3 Claims, No Drawings

OXIDATION CATALYSTS

REFERENCE TO RELATED APPLICATIONS

This is a continuation-in-part of our earlier application Ser. No. 778,658, filed Mar. 17, 1977, now abandoned, which is a divisional of Ser. No. 602,343, filed Aug. 6, 1975, now U.S. Pat. No. 4,052,418, issued Oct. 4, 1977.

BACKGROUND OF THE INVENTION

U.S. Pat. No. 3,780,011 to Pullukat, et al. discloses use of catalysts containing chromium, titanium, boron, or vanadium. Also known is the use of catalysts containing antimony and vanadium. The above prior art neither discloses nor suggests the catalytic composition of the present invention which contains at least one element selected from the group consisting of an alkali metal, zinc, cadmium, arsenic, copper, cerium, thorium, iron, tin and manganese in addition to vanadium and boron.

U.S. Pat. No. 4,003,978 to Shiraishi, et al. discloses use of catalysts containing chromium, at least one element selected from the group consisting of tin, antimony, vanadium, cobalt, silver, zinc, nickel, titanium, molybdenum, tungsten, phosphorus, boron, germanium, and zirconium; U.S. Pat. No. 3,554,931 to Brown, et al. discloses use of catalysts containing antimony, vanadium, and optionally at least one element selected from the group consisting of tin, titanium, chromium, manganese, iron, cobalt, nickel, copper, zinc, molybdenum, cadmium, tungsten or thorium; U.S. Pat. No. 3,579,574 to Teunis van der Meer discloses use of a catalyst containing antimony and vanadium or vanadium, antimony and at least one element selected from the group consisting of iron, manganese, chromium, cobalt, nickel, copper, zinc, cadmium, tungsten and thorium; U.S. Pat. No. 4,010,238 to Shiraishi, et al. discloses use of catalysts containing vanadium and at least one element selected from the group consisting of copper, zinc, tin, lead, titanium, phosphorus, chromium, iron, cobalt and nickel; and U.S. Pat. No. 3,424,781 to Capp, et al. discloses use of catalysts containing antimony, chromium and vanadium. Nowhere do any of these patents suggest that arsenic may be successfully incorporated as an essential catalytic component when antimony, zinc or chromium is present.

U.S. Pat. No. 3,704,317 to Yamashita, et al. discloses use of catalysts containing vanadium and one or more of the secondary elements lithium, boron, silicon, chromium, iron, nickel, zinc, zirconium, niobium, rubidium, rhodium, tantalum, and bismuth. In the Specific Embodiments portion of this reference is exemplified use of catalysts containing vanadium and single promoters of lithium, chromium, rhodium, zinc, boron, zirconium, bismuth, nickel, niobium, palladium and tungsten. Nowhere does Yamashita, et al. show the effectiveness of combining, for example, zinc and niobium. There is nothing in the patent to lead one to specifically select boron, zinc, tungsten and niobium from the large class of listed metals stated to have catalytic value.

U.S. Pat. No. 3,544,616 to Grasselli, et al. discloses use of a catalyst containing as essential catalytic components uranium and arsenic promoted by molybdenum, boron, vanadium, tin, nickel, bismuth, chromium, iron, manganese, zinc, tungsten, antimony, cerium, cobalt or rhenium. Uranium, an integral component in the Grasselli, et al. catalyst, is nowhere listed among the ingredients of the claimed catalyst composition of the present invention.

U.S. Pat. No. 3,855,318 to Nakajima, et al. discloses use of catalysts containing vanadium, iron, and at least one oxide of magnesium, titanium, manganese, beryllium or boron. In accordance with the present invention, boron and iron are not combined as catalytic ingredients. One would not be led to delete the iron from the catalyst of Nakajima with an expectation of success.

U.S. Pat. No. 3,907,919 to Ching-Tsan Lo discloses a catalyst containing a vanadate of Group IVA and/or VA metals promoted by compounds of Group VB, VIB or Group VIII of the Periodic Table. In view of the vast list of possible catalytic ingredients described in the Lo patent, one would not be led to the specifically defined catalyst composition of the present invention.

U.S. Pat. No. 2,954,385 to Burney, et al. discloses use of catalysts containing vanadium and at least one element selected from the group consisting of phosphorus, aluminum, titanium, iron, cobalt, zinc, copper, nickel, magnesium, manganese, silver, antimony and bismuth. In accordance with the preferred procedure of the present invention, when antimony and zinc are present as catalytic components arsenic must also be present. British Pat. No. 1,011,678 to Mihail discloses use of catalysts containing vanadium, boron and at least one of cerium, uranium and tin. In accordance with the present invention, when boron is present as a catalytic component cerium and tin may not be present.

U.S. Pat. No. 4,075,231 to Dolhyj, et al. discloses the preparation of phthalic anhydride from orthoxylene using coated catalysts containing Fe, Cr, Ni, Co, Mn, Cu, Ag, Bi, Zn, Mo, W or mixture thereof, boron, antimony, or mixture thereof, vanadium and oxygen. U.S. Pat. No. 4,076,731 to Dolhyj, et al. discloses the preparation of phthalic anhydride using a coated catalyst containing vanadium, oxygen, and boron, antimony, or mixture thereof. The catalyst composition of the present invention cannot be constructed from a reading of these patents.

SUMMARY OF THE INVENTION

It has been discovered in the process for the production of maleic anhydride by the oxidation of n-butane, n-butenes, butadiene or a mixture thereof with molecular oxygen in the vapor phase at an elevated temperature of about 300° C. to about 600° C. in the presence of a catalyst comprising the combined oxides of vanadium and at least one element selected from the group consisting of boron, niobium, tantalum, antimony, tungsten and chromium.

The most significant aspect of the present invention is the catalyst. The catalyst, as noted, may be optionally promoted with additional elements to enhance its activity, stability and selectivity. Preferred catalysts are described by the following formula:

$$A_aV_bD_cO_x$$

wherein
A is at least one element selected from the group consisting of an alkali metal, zinc, cadmium, phosphorus, arsenic, copper, cerium, thorium, tin, manganese, iron and uranium;
D is at least one element selected from the group consisting of boron, niobium, tantalum, antimony, tungsten and chromium;
and wherein a is 0 to 5;

b and c are 0.1 to 10; and x is the number as determined by the combined valence requirements of elements other than oxygen present in the catalyst.

The present invention is an improved process for the production of maleic anhydride from four-carbon paraffins by the use of a new catalyst. Maleic anhydride is produced in a simple manner at a low cost by the oxidation of inexpensive paraffins. The stability and activity of the catalyst is improved; and unlike most processes that deal with the catalytic vapor oxidation of paraffins to produce maleic anhydride, the catalyst composition does not require phosphorus as an essential element. The process of the present invention is especially effective in the production of maleic anhydride from n-butane in good yields. Also, the catalysts of the present invention are useful in the production of phthalic anhydride from xylenes. Especially preferred catalysts are described by the formula:

$$A_a V_b D_c O_x$$

wherein

A is at least one element selected from the group consisting of an alkali metal, zinc, cadmium, arsenic, copper, cerium, thorium, iron, tin and manganese;

D is at least one element selected from the group consisting of boron, niobium, tantalum, and tungsten;

and wherein a is a positive number less than or equal to 5;

b and c are 0.1 to 10; and x is a number as determined by the combined valence requirements of the elements other than oxygen present in the catalyst;

and wherein when A is cerium, tin and iron, zinc and copper, D is not boron.

Desirable results are achieved using a catalyst wherein D is boron; a catalyst wherein D is niobium; a catalyst wherein D is tungsten; or a catalyst wherein b and c are 0.1 to 5.

Excellent results are achieved using a catalyst composition having the empirical formula:

$$A_a V_b D_c O_x$$

wherein

A is arsenic and at least one element selected from the group consisting of an alkali metal, zinc, cadmium, copper, cerium, thorium, manganese, and iron;

D is at least one element selected from the group consisting of chromium and antimony;

and wherein a is a positive number less than or equal to 5;

b and c are 0.1 to 5; and x is a number as determined by the combined valence requirements of the elements other than oxygen present in the catalyst.

Especially preferred catalysts within this formula are catalysts wherein A is arsenic and zinc; and catalysts wherein D is antimony. Also preferred is a catalyst composition described by the following formula:

$$A_a V_b D_c O_x$$

wherein

A is at least one element selected from the group consisting of zinc, potassium and arsenic; and D is at least one element selected from the group consisting of boron, niobium, tantalum and tungsten;

and wherein a is a positive number less than or equal to 5;

b and c are 0.1 to 10; and x is a number as determined by the combined valence requirements of elements other than oxygen present in the catalyst; and wherein when A is zinc, D is not boron.

The catalysts may be prepared by a number of known methods. The catalysts are conveniently prepared by digesting oxides or salts of the various ingredients of the catalysts in concentrated hydrochloric acid. Other methods such as combining the oxides or nitrates, are also acceptable. The most preferred preparation is described in the Specific Embodiments.

The catalysts may be used alone or a support could be employed. Suitable supports include silica, alumina, Alundum, silicon carbide, boron phosphate, zirconia and the like. The catalysts are conveniently used in a fixed-bed reactor using tablets, pellets or the like or in a fluid-bed reactor using a catalyst preferably having a particle size of less than about 300 microns.

The process for preparing maleic anhydride by reacting the hydrocarbon with molecular oxygen in the vapor phase in the presence of a catalyst is known. The hydrocarbon reacted by the process of the present invention may be n-butane, n-butenes, butadiene or mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of the hydrocarbon to molecular oxygen may range from about 2 to about 30 moles of oxygen per mole of hydrocarbon. The higher oxygen ratios are associated with fixed-bed reactors and are used to avoid the explosive range of the reactants. Preferred oxygen ratios are about 4 to about 20 moles per mole of hydrocarbon.

The reaction temperature may vary widely and is dependent upon the particular hydrocarbon and catalyst employed. Suitably, a temperature within the range of about 300° C. to about 600° C. gives the best results. The reaction can be conducted to atmospheric, superatmospheric or subatmospheric pressure.

SPECIFIC EMBODIMENTS

Examples 1 to 17

Preparation of maleic anhydride using various catalysts of the invention.

Catalysts of the invention were prepared as follows:

EXAMPLE 1

$$Zn_{0.2}V_1B_{1.2}O_x$$

45.5 g. of vanadium pentoxide was digested in 295 cc. of concentrated HCl and the mixture was heated on a hot plate with constant stirring for about one-half hour, an aqueous solution containing 13.6 g. of zinc chloride was added. Heating and stirring was continued about 15 minutes. An aqueous slurry containing 37.1 g. of boric acid was added to the mixture and heated with constant stirring until the mixture solidified. The catalyst was dried at about 120° C.

EXAMPLE 2

$Zn_{0.2}V_1B_1Sb_{0.2}O_x$ 22.4 g. of vanadium pentoxide was digested in 295 cc. of concentrated HCl and refluxed for 4 hours, 7.29 g. of antimony trioxide was added to this solution, followed by the addition of an aqueous solution containing 15.5 g. of boric acid, and an aqueous solution containing 6.8 g. of zinc chloride. The mixture was refluxed for 2 hours and was slowly evaporated to dryness.

EXAMPLE 3

$V_1Nb_1Sb_{0.2}O_x$

A vanadium-containing solution was prepared in the same manner was Example 2.

33.3 of niobium pentoxide was mixed with 6.1 g. of antimony metal powder in $H_2O$. HCl was slowly added to this solution with constant stirring and the bulk was added to the vanadium-containing solution. The mixture was refluxed for 6 hours. The color changed to pale-green. The catalyst was evaporated to dryness.

EXAMPLE 4

$V_{1.0}W_{1.2}Zn_{0.2}O_x$

A vanadium-containing solution was prepared in the same manner as Example 2.

75.0 g. of tungstic acid was added to 3.27 g. of zinc metal powder in water, the bulk color changed to blue; dilute HCl was added. This mixture was added to the vanadium-containing solution. The color changed from blue to yellowish-green. The bulk was slowly evaporated to dryness.

EXAMPLE 5

$Zn_{0.2}V_{1.0}Sb_{1.2}As_{0.1}O_x$

This catalyst was prepared in the same manner as Example 2 using these compounds in amounts as follows:
298 cc HCl (conc.)
22.7 g. of $V_2O_5$
6.8 g. of $ZnCl_2$
43.7 g. of $Sb_2O_3$
3.8 g. of $H_3AsO_4 \cdot \frac{1}{2}H_2O$

EXAMPLE 6

$Zn_{0.2}V_1Nb_{1.2}O_x$

This catalyst was prepared in the same manner as Example 5 except the antimony trioxide and arsenic acid were replaced by 39.9 g. of niobium pentoxide.

EXAMPLE 7

$K_{0.02}[Zn_{0.2}V_1Nb_{1.2}O_x]$

This catalyst was prepared by impregnating the catalyst of Example 6 as follows: 5.5 g. of the catalyst were heated with $2.4 \times 10^{-4}$ g. of potassium hydroxide in 1.5 mls. of distilled $H_2O$.

EXAMPLES 8 TO 17

The catalyst were prepared in the same manner as shown above using the appropriate ratio of ingredients.

The catalysts prepared above were ground and screened to recover these particles of 20 to 32 mesh size. A portion of these catalyst particles were placed in a 5 cc. fixed-bed reactor constructed of a length of 12.7 cm. stainless steel tubing having a 1.0 cm. inside diameter and heated under a flow of air for 16 hours at 290° C.

The reactor was heated to the reaction temperature and a feed of 1 n-butane/50 air was fed over the catalyst at an apparent contact time of 1.0 second. The reactor was run under the reaction conditions for two hours to pre-condition the catalyst. The reactor effluent was collected and analyzed by gas chromatography.

The results are stated in terms of single pass yield which is defined as $$\frac{\text{Moles of Maleic anhydride obtained}}{\text{Moles of n-butane in the feed}} \times 100$$

and the total conversion defined as $$\frac{\text{Moles of n-butane reacted}}{\text{Moles of n-butane in the feed}} \times 100$$

and the selectivity defined as $$\frac{\text{Single Pass Yield}}{\text{Total Conversion}} \times 100$$

The experimental results are shown in the Table below.

TABLE

Preparation of Maleic Anhydride from n-Butane

| EXAMPLE | CATALYST | REACTION TEMP. °C. | N-BUTANE CONVERSION | SINGLE PASS YIELD | SELECTIVITY |
|---|---|---|---|---|---|
| 8 | $Zn_{0.2}V_{1.0}B_{1.2}O_x$ | 450 | 18.2 | 10 | 55 |
| 9 | $Zn_{0.2}V_{1.0}B_{1.2}O_x$ | 500 | 21.2 | 14 | 66 |
| 10 | $Zn_{0.2}V_1B_1Sb_{0.2}O_x$ | 480 | No data | 1.2 | No data |
| 11 | $Zn_{0.2}V_1B_1Sb_{0.2}O_x$ | 540 | 6.1 | 4.6 | 86.0 |
| 12 | $V_1Nb_1Sb_{0.2}O_x$ | 450 | No data | 3.8 | No data |
| 13 | $V_{1.0}W_{1.2}Zn_{0.2}O_x$ | 450 | No data | 1.6 | No data |
| 14 | $Zn_{0.2}V_{1.0}Sb_{1.2}As_{0.1}O_x$ | 400 | 98.7 | 7.2 | 7.3 |
| 15 | $Zn_{0.2}V_{1.0}Nb_{1.2}O_x$ | 450 | 58.6 | 22.5 | 38.5 |
| 16 | $Zn_{0.2}V_{1.0}Nb_{1.2}O_x$ | 500 | 93.6 | 32 | 34.2 |
| 17 | $K_{0.02}[Zn_{0.2}V_{1.0}Nb_{1.2}O_x]$ | 500 | 80.8 | 12.6 | 15.6 |

We claim:
1. A catalyst composition having the empirical formula:

$$A_aV_bD_cO_x$$

wherein
A is arsenic and at least one element selected from the group consisting of an alkali metal, zinc, cadmium, copper, cerium, thorium, manganese and iron;
D is at least one element selected from the group consisting of chromium and antimony;
and wherein
a is a positive number less than or equal to 5;
b and c are 0.1 to 5; and
x is a number as determined by the combined valence requirements of the elements other than oxygen present in the catalyst.

2. The catalyst of claim 1 wherein A is arsenic and zinc.

3. The catalyst of claim 1 wherein D is antimony.